(12) United States Patent
Flohr et al.

(10) Patent No.: US 9,204,847 B2
(45) Date of Patent: Dec. 8, 2015

(54) METHOD, IMAGE DATA RECORD PROCESSING FACILITY, X-RAY SYSTEM AND COMPUTER PROGRAM PRODUCT FOR CORRECTING IMAGE DATA OF AN EXAMINATION OBJECT

(75) Inventors: Thomas Flohr, Uehlfeld (DE); Bernhard Schmidt, Nürnberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 781 days.

(21) Appl. No.: 13/372,936

(22) Filed: Feb. 14, 2012

(65) Prior Publication Data

US 2012/0207270 A1    Aug. 16, 2012

(30) Foreign Application Priority Data

Feb. 15, 2011    (DE) .......................... 10 2011 004 120

(51) Int. Cl.
*A61B 6/00*    (2006.01)
*G06T 5/50*    (2006.01)
*A61B 6/03*    (2006.01)

(52) U.S. Cl.
CPC .............. *A61B 6/4014* (2013.01); *A61B 6/482* (2013.01); *A61B 6/5258* (2013.01); *G06T 5/50* (2013.01);
(Continued)

(58) Field of Classification Search
CPC ...... A61B 6/482; A61B 6/032; A61B 6/4014; A61B 6/5258; G06T 2207/20224; G06T 5/50; G06T 2207/10081; G06T 2207/10116
USPC ............................................................ 378/5
See application file for complete search history.

(56) References Cited

U.S. PATENT DOCUMENTS 4,658,410 A    4/1987    Haendle
5,774,519 A *  6/1998    Lindstrom et al. .............. 378/18
(Continued)

FOREIGN PATENT DOCUMENTS

CN    1502309 A    6/2004
CN    1647767 A    8/2005
(Continued)

OTHER PUBLICATIONS

Lell et al., Dual energy CTA of the supraaortic arteries: Technical improvements with a novel dual source CT system, available on line Oct. 9, 2009, European Journal of Radiology, v76, pp. e6-e12.*
(Continued)

*Primary Examiner* — David J Makiya
*Assistant Examiner* — John Corbett
(74) *Attorney, Agent, or Firm* — Harness, Dickey & Pierce, P.L.C.

(57) ABSTRACT

A method and an image data record processing facility are disclosed for correcting image data of an examination object, which includes a first image data record obtained using a first X-ray energy and a second image data record obtained using a second X-ray energy. In this process, a corrected image data record is generated by subtracting from image point values at certain image point positions of the first image data record, image point values, which are assigned to the corresponding image point positions in the second image data record, multiplied by a weighting factor. The weighting factor here is selected as a function of the first X-ray energy used and the second X-ray energy used so that on subtraction a calcium component is removed from the image point values. A method for generating image data and an X-ray system having such an image data record processing facility are also described.

20 Claims, 4 Drawing Sheets

(52) U.S. Cl.
CPC ....... *A61B 6/032* (2013.01); *G06T 2207/10081* (2013.01); *G06T 2207/10116* (2013.01); *G06T 2207/20224* (2013.01)

(56) References Cited

U.S. PATENT DOCUMENTS

| | | | |
|---|---|---|---|
| 6,421,412 | B1 | 7/2002 | Senzig |
| 7,190,757 | B2 | 3/2007 | Crawford |
| 7,457,450 | B2 | 11/2008 | Bruder et al. |
| 7,873,141 | B2 | 1/2011 | Imai et al. |
| 2003/0215120 | A1 | 11/2003 | Uppaluri et al. |
| 2004/0102688 | A1 | 5/2004 | Walker et al. |
| 2005/0111718 | A1* | 5/2005 | MacMahon et al. .......... 382/130 |
| 2005/0163283 | A1 | 7/2005 | Bruder et al. |
| 2007/0249933 | A1 | 10/2007 | Krauss |
| 2008/0144764 | A1* | 6/2008 | Nishide et al. .................... 378/5 |
| 2008/0260092 | A1* | 10/2008 | Imai et al. ......................... 378/5 |
| 2011/0280458 | A1* | 11/2011 | Flohr et al. .................... 382/131 |

FOREIGN PATENT DOCUMENTS

| | | |
|---|---|---|
| CN | 101044988 A | 10/2007 |
| CN | 101249000 A | 8/2008 |
| CN | 1504931 B | 5/2010 |
| DE | 102004004295 A1 | 8/2005 |
| DE | 102006015454 A1 | 10/2007 |
| DE | 102006040935 A1 | 3/2008 |
| DE | 102007053511 A1 | 5/2008 |

OTHER PUBLICATIONS

Yu et al., Image quality optimization and evaluation of linearly mixed images in dual-source, dual-energy CT, 2009, Medical Physics, vol. 36, No. 3, pp. 1019-1024.*
Chinese Office Action and English translation thereof dated Jan. 2, 2014.
German Office Action for German Application No. DE 10 2011 004 120.6, and English translation thereof.
German Priority Document for German Application No. DE 10 2011 004 120.6 (Not Yet Published), noted as present.

* cited by examiner

METHOD, IMAGE DATA RECORD PROCESSING FACILITY, X-RAY SYSTEM AND COMPUTER PROGRAM PRODUCT FOR CORRECTING IMAGE DATA OF AN EXAMINATION OBJECT

PRIORITY STATEMENT

The present application hereby claims priority under 35 U.S.C. §119 to German patent application number DE 10 2011 004 120.6 filed Feb. 15, 2011, the entire contents of which are hereby incorporated herein by reference.

FIELD

At least one embodiment of the invention generally relates to a method for correcting image data of an examination object, wherein the image data comprises a first image data record, which was obtained by way of an X-ray system using a first X-ray energy, and a second image data record, which was obtained by way of the X-ray system using a second X-ray energy.

At least one embodiment of the invention also generally relates to a method for generating image data, wherein an X-ray system is used to perform a first measurement with a first energy, on the basis of which a first image data record is generated, and then to perform a second measurement with a second energy, on the basis of which a second image data record is generated, and then a corrected image data record is generated according to the correction method.

At least one embodiment of the invention also generally relates to an image data record processing facility, for correcting image data of an examination object and an X-ray system with such an image data record processing facility as well as a corresponding computer program product.

BACKGROUND

Measurements in which image data sets of the examination object are recorded with different X-ray energies, are generally referred to as what are termed dual energy procedures. Since the attenuation of the X-ray beams in the different materials is a function of energy, it is possible to use this measurement procedure to obtain additional information compared with a measurement using just one X-ray energy. This information can be used to differentiate more easily between different materials in the beam path between the X-ray source and the X-ray detector.

A typical example of the application of a dual energy procedure is CT angiography (CT=X-ray computed tomography). For such an examination a contrast agent is administered to the patient shortly before the start of the CT measurement, so that at the time of the recording the vessels or vessel lumina to be examined contain contrast agent. A contrast agent containing iodine is generally used, which because of its high atomic number results in significant attenuation of the X-ray radiation and therefore good vessel contrast. It is therefore generally possible to assess the vessel state effectively. It becomes more problematic when already calcified plaques have formed in the vessel walls. The limited resolution of the CT system and the CT procedure per se mean that the known effect of "calcium blooming" frequently results. This effect causes calcifications to appear much larger than they actually are in the CT image data records. Stenoses produced by the calcified plaques therefore appear much larger than they really are so that the degree of stenosis is overestimated.

To avoid this problem, it is possible to differentiate between calcium and iodine with the aid of dual energy CT examinations, the differentiation having been made up to now on the basis of what is known as the dual energy ratio. To this end the image point values, assigned respectively to identical image point positions in both image data records generated with different X-ray energies, are divided by one another. Image points in the context of embodiments of the present invention refer to the individual voxels and pixels of the image data records. The image point values are therefore the intensity values or the like for the individual voxels and pixels, which are generally determined by means of appropriate reconstruction procedures based on the measured detector values. Generally in X-ray procedures, which include CT procedures, these values are given in the form of Hounsfield values (HU values). Similarly the image point positions in the context of the present invention refer to the voxel and pixel positions. To determine the dual energy ratio, the HU values of the low-energy image are generally divided by the HU values of the high-energy image based on the voxels or pixels. The voxel or pixel in question is then assigned to a material, in this instance either calcium or iodine, based on this dual energy ratio. However problems still arise here due to calcium blooming. If calcium and iodine are directly adjacent to one another, the HU values of the iodine voxels close to the boundary with the bone are falsified by the nearby calcium due to the blooming. This results typically in a rise in the HU values as a function of the X-ray tube voltage, i.e. as a function of the X-ray energy, and therefore also an undesirable change in the dual energy ratio. If the threshold value used to differentiate between calcium and iodine is set precisely at a value between calcium and iodine, if the calcification is extensive enough, the degree of stenosis may be correctly determined. However the remaining voxels in the boundary region with the calcium are falsified, which can among other things cause vessel parts to be eliminated in the image data, in other words to be no longer visible. If however a lower threshold value is used, the remaining image looks better visually but the stenosis is again overestimated, because too high a calcium component remains in the image data.

Another possibility for reducing an overestimate of the degree of stenosis due to calcium blooming is to record CT data as reference image data before administering a contrast agent. This reference image data can then be subtracted from the CT angiography data. Since calcium blooming results in both data records, the effects are canceled out on subtraction and only the lumen without calcification remains. But this procedure has a number of disadvantages. Firstly an additional measurement is required. Secondly there is a significant problem in that a long time interval has to be left between the two measurements due to the waiting time until the contrast agent has spread in the body of the patient. Complex registration (i.e. geometrical matching) of the image data is therefore required to at least reduce motion artifacts, as otherwise the results may be falsified.

SUMMARY

At least one embodiment of the invention provides an improved method and an improved image data record processing facility for correcting image data from a dual energy measurement, which in the simplest possible manner allow the effect of calcium blooming to be reduced and the degree of stenosis to be determined more precisely, particularly in CT angiography.

At least one embodiment is directed to a correction method and/or an image data record processing facility.

At least one embodiment of the inventive method also uses a dual energy measurement procedure, in other words a first image data record is generated using a first X-ray energy and a second image data record is generated using a second X-ray energy that is different from the first X-ray energy. In contrast to the dual energy correction procedures known until now however, the dual energy ratio is not determined to reduce calcium blooming but a corrected image data record is generated by subtracting from the image point values, i.e. the intensity values of the individual pixels and voxels, at certain image point positions of the first image data record, the image point values at the corresponding image point positions of the second image data record, multiplied by a weighting factor. The weighting factor here is selected as a function of the first X-ray energy used and the second X-ray energy used so that on subtraction a calcium component is removed from the image point values. In a further inventive method step, which can be employed as an alternative or in addition to the application of noise-reducing filters, a combination image data record (also referred to below as a mixed image) is generated from the first image data record and the second image data record. To generate the corrected image data record, the image point values of the second image data record multiplied by a weighting factor are then only subtracted from the image point values at the corresponding image point positions of the first image data record at the image positions where image point values of the combination image data record are greater than a limit value. The limit value or threshold here can be set so that at image points, which are to be assigned for example to soft tissue without contrast agent and whose intensity values are therefore smaller, no change is made by subtraction. The information from the subtraction image is only used for image points with sufficiently high intensity values, i.e. above the threshold, for example for voxels in the region of vessels filled with contrast agent, where the problem of calcium blooming specifically occurs.

The physical attributes and the attributes of the X-ray measurement principle, in particular the CT measurement principle, mean that the weighting factor, which is a function of the energy combination, is virtually independent of the calcium concentration in a certain voxel, i.e. at a certain image point position. It therefore comes about automatically that the calcium component is removed from the image point value not only for the image points which actually contain calcium but that the image point values of image points, which are adjacent to calcified structures and were therefore falsified by calcium blooming, are also corrected. Other structures—such as for example the image points of the vessels filled with contrast agent—are maintained with this method, since cancelation does not result on subtraction using the predefined weighting factor due the different attenuation behavior in contrast to calcium structures.

Since subtraction of the image points therefore also causes the calcium components produced by blooming to be removed, no further calcium blooming problems occur compared with correction based on the dual energy ratio. However it is not necessary to perform an additional reference measurement a relatively long time before administration of the contrast agent. This avoids motion artifacts as far as possible.

An inventive image data record processing facility of at least one embodiment can be used to perform the method. This must have an image data interface, to transfer the image data records, and an interface to transfer a weighting factor, for example based on user input or from a memory, in which the weighting factor is stored. The image data record processing facility also requires a correction unit, which, to generate a corrected image data record, is configured to subtract from image point values at certain image point positions of the first image data record, image point values at the corresponding image point positions of the second image point data record, multiplied by the weighting factor, with the first weighting factor being selected as a function of the first X-ray energy and the second X-ray energy used so that on subtraction a calcium component is removed from the image point values.

At least one embodiment of the inventive correction method can be used directly in the context of an inventive method for generating image data of an examination object, with an X-ray system being used to perform a first measurement with a first energy, on the basis of which a first image data record is generated, and to perform a second measurement with a second energy, on the basis of which a second image data record is generated, and a corrected image data record then being generated from this first and second image data record using at least one embodiment of the inventive correction method.

An inventive image data record processing facility of at least one embodiment can correspondingly also be part of an X-ray system having at least one X-ray source and at least one detector system for acquiring projection data records of an examination object, in particular of a CT system. In other words the image data record processing facility can be installed for example on a control and evaluation processor of the X-ray system. In principle however such an image data record processing facility can also be implemented in other processor units, which are connected for example to such an X-ray system by way of a network for the transfer of data or can be supplied in another way with corresponding image data records.

In particular the correction unit of the image data record processing facility can be implemented as a software module on an appropriate processor. The image data interface and the interface for transferring the weighting factor can also be implemented in purely software form, as long as it is only necessary to transfer the data records and weighting factor from other preprocessing facilities or memories implemented on the same processor unit. In principle these interfaces can however also be implemented as combined hardware/software interfaces, to allow an external transfer, for example with the aid of software components of specifically configured hardware interfaces.

The image data record processing facility also generally has an output interface to output the corrected image data record, for example to an appropriate memory and/or directly to an operator on a screen or printer. This output interface can also be a purely software interface or a combined hardware/software interface.

A largely software-based implementation has the advantage that already existing image data record processing facilities can be retrofitted simply by way of a software update, in order to operate in the inventive manner. To this extent the object is also achieved by a computer program product, which can be loaded directly into a memory of a programmable image data record processing facility, having program code segments to execute all the steps of the inventive correction method, when the program is executed in the image data record processing facility.

Further advantageous embodiments and developments of the invention will emerge from the dependent claims and the description which follows. The claims of one category here can also be developed in the same way as the dependent claims of another claim category.

The first X-ray energy is preferably selected so that it is lower than the second X-ray energy, in other words the first image data record is then what is termed a low-energy image data record and the second image data record a high-energy image data record. The X-ray energy is generally characterized by the acceleration voltage of the X-ray tube and correspondingly generally given using the unit kV. Standard energy combinations used in dual energy procedures are 80 kV for the low X-ray energy and 140 kV for the higher energy or 100 kV for the low energy and 140 kV for the higher energy.

In one preferred development of the method before the corrected image data record is generated, the image point values of the first image data record are each displaced by a first correction value and/or the image points of the second image data record are each displaced by a second correction value. Such a displacement means that certain materials remain almost unchanged with the correction. It is also possible for the two correction values to be identical.

In one preferred development for example the first correction value can be selected so that it corresponds roughly to a mean image point value of a base material in the first image data record. The second correction value can accordingly correspond roughly to a mean image point value of the base material in the second image data record. The base material here refers to the material that occurs most frequently in the recorded region of the examination object and therefore forms the "background structure" of the image.

For example in a head recording the base material can be the soft tissue of the brain, while the vascular tissue, the calcium components and the vascular lumen filled with contrast agent stand out against this base material and form the structures to be examined. With such a head recording the first correction value selected could be a Hounsfield value for example, which corresponds roughly to a mean Hounsfield value for soft tissue with the first X-ray energy. The second correction value is then selected so that it corresponds roughly to the mean Hounsfield value of the soft tissue with the second X-ray energy. Since soft tissue is generally not or scarcely a function of the energy or X-ray voltage, the first and second correction values can be set as identical here. In this instance a CT value of perhaps approx. 40 HU is preferably selected as the correction value for soft tissue. Displacing the image point values of the first image data record and the second image data record by such a correction value of CT=40 HU ensures that, as the base material, the soft tissue then has a CT value of 0 HU in each instance. This ensures that the weighting factor has no or only little influence on the image point values of the soft tissue on subtraction and the image points are also displayed almost unchanged after subtraction.

To reduce the noise in the subtraction image, i.e. in the corrected image data record, it is advantageous to implement noise reduction measures. In one preferred variant before subtraction noise-reducing filters are applied to the image data records, such as for example non-linear filters or iterative methods. This significantly reduces the noise in the corrected image data record.

It is particularly preferable here at the other image points of the corrected image data record for the image point values at the corresponding image point positions of the combination image data record simply to be taken over as the image point values. In other words with this method information from the mixed image and the subtraction image of the two image data records is combined.

To generate the combination image data record the image points at certain image point positions of the first image data record and the image point values at the corresponding image point positions of the second image data record are preferably added together. Weighted addition is also possible here.

At least one embodiment of the inventive method can be used in principle for image data records generated using any X-ray systems, i.e. for example also using X-ray devices which generate image data in the form of simple projection recordings. However at least one embodiment of the method is particularly preferably used when the X-ray system is first used to record projection data records and these are then used to reconstruct the image data records, in order thus to be able to map the interior of the object to be examined in three dimensions. Such image data records then consist for example of a three-dimensional matrix of voxels, and any sectional images with individual pixels can be generated therefrom. The X-ray system is therefore preferably a CT system and/or an angiography device. The image data record processing facility should then have a measurement data interface for transferring projection data records obtained using the X-ray system and a reconstruction unit, which is configured to reconstruct the first image data record from a projection data record of a first measurement and the second image data record from a projection data record of a second measurement.

It has proven that the appropriate weighting factor is determined not only as a function of the energy combination but also advantageously as a function of the X-ray system or X-ray system type, with which the measurement data was acquired to obtain the image data. In other words a system-specific or device-specific weighting factor is selected. Not only does "X-ray system type" within the meaning of the present invention refer to the basic nature of the X-ray system (i.e. simple X-ray device, CT system or angiograph, etc.) but X-ray systems of the same nature but made by different manufacturers and/or from different series are also understood to be different X-ray system types.

In one example variant such a system-specific or device-specific weighting factor can be determined by experiment with the aid of image data, which is based on measurement data acquired with the same X-ray system or with an X-ray system of the same X-ray system type. Additionally or alternatively appropriate simulations of such measurements can also be performed using a corresponding X-ray system or X-ray system type and be used to determine the weighting factor. Once the weighting factor has been determined, it can be stored in a memory of the respective X-ray system or the image data record processing facility for this X-ray system, so that it can optionally also be retrieved automatically from the memory when calculating the corrected image data record.

BRIEF DESCRIPTION OF THE DRAWINGS

The invention is described in more detail again below based on example embodiments with reference to the accompanying figures, in which.

Figure 1:
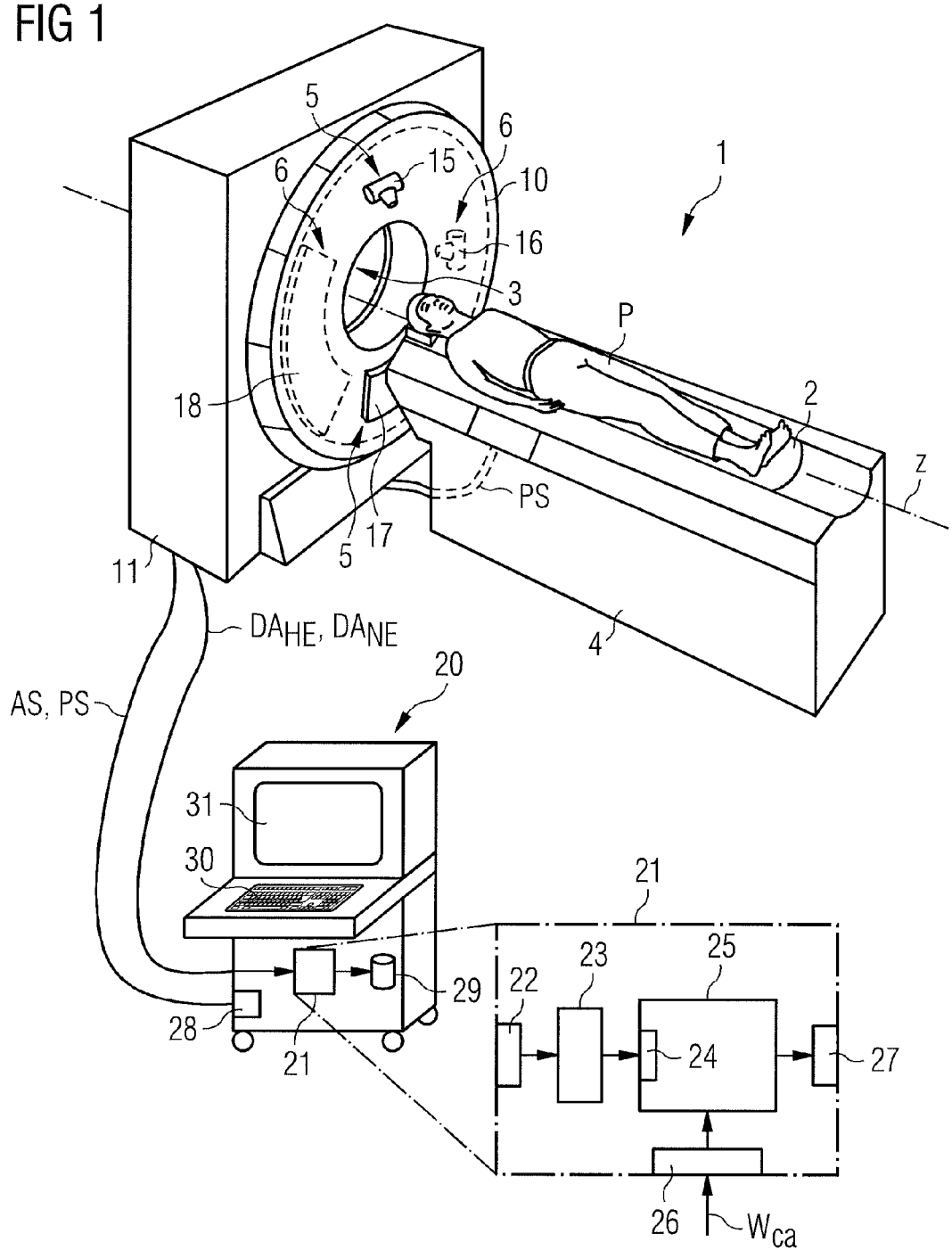
FIG. 1 shows a highly schematic diagram of a computed tomography system with an inventive image data record processing facility.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic diagram of a computed tomography system 1 with an inventive image data record processing facility 21. The CT system 1 here includes a standard dual source scanner 11, in which two data acquisition systems 5, 6, each having an X-ray source 15, 16 with a detector 17, 18 opposite each X-ray source 15, 16, travel around a measurement chamber 3 on a gantry 10. In front of the scanner 11 is a patient support facility or patient table 4, the upper part 2 of which can be displaced with an examination object P positioned thereon, in this instance a patient, relative to the scanner 11 along the z-direction, which corresponds to the system axis z longitudinally through the measurement chamber 3, so that the patient P is moved through the measurement chamber 3 relative to the data acquisition systems 5, 6. The scanner 11 and patient table 4 are activated by a control facility 20, from which control data PS for table positioning and control data AS for the data acquisition systems 5, 6 is output by way of a standard interface 28, to activate the CT system 1 according to predefined measurement protocols in the conventional manner.

It is in principle possible here to move the patient along the z-axis and allow the X-ray sources 15, 16 to travel round at the same time, so that a helical path results for the X-ray sources 15, 16 relative to the patient P during the measurement. Volume data from the body of the patient is thus recorded. In another, sequential, measurement method the patient P is moved along in steps in the z-direction and when stationary the X-ray sources 15, 16 travel round in each instance through a certain angular distance (generally at least 180°), in order to generate sufficient projections in a certain sectional image plane. With this variant volume data is thus generated in the form of individual slices perpendicular to the system axis z.

With the described dual source scanner 11 the two X-ray sources 15, 16 respectively are set so that they operate with different X-ray tube voltages and therefore emit X-ray radiation of different energy. This means that two projection data records are generated at the same time during a measurement, specifically a low-energy projection data record DANE and a high-energy projection data record DAHE.

It should be noted that instead of the system shown in FIG. 1 any other computed tomography system can be also be used to generate projection data records DANE, DAHE for an embodiment of the inventive method. On the one hand it is possible to use scanners with just one data acquisition system and set the X-ray tube voltage differently in two measurements in quick succession. The scanner can also be structured differently and for example have a circular detector ring instead of a detector that travels with the X-ray tube on the opposite side, the detector elements of said detector ring being read out appropriately for the circulating X-ray source. Other structural variants are also possible.

The raw data or projection data records DANE, DAHE acquired thus by way of the data acquisition systems 5, 6 are then transferred to the control facility 20. This control facility 20 is equipped here with an inventive image data record processing facility 21, which is shown enlarged again in FIG. 1 with its components.

The image data record processing facility 21 is configured so that it has a measurement data interface 22 for transferring the projection data records DANE, DAHE, which transfers these to a reconstruction unit 23, which generates a low-energy image data record correspondingly from the low-energy projection data record DANE and a high-energy image data record from the high-energy projection data record DAHE.

The image data records are then transferred to an image data interface 24 of a correction unit 25, which generates the corrected image data record in the inventive manner. The procedure for this is described again below in detail. To this end the correction unit transfers a weighting factor wCa by way of a further interface 26.

The finished corrected image data records can then be stored by way of an output interface 27 for example in a memory 29 or be output for a user in the usual manner on a screen 31 of the control facility 20. The interface 26 can moreover be configured so that it transfers the weighting factor wCa from a user interface, for example a keyboard 30, by way of which a user inputs the weighting factor wCa. Likewise this interface 26 can also transfer the weighting factor wCa from a memory, for example the memory 29, in which weighting factors for certain X-ray energy combinations have already been stored.

At least the reconstruction unit 23 and the correction unit 25 are configured here in the form of software on a processor or a number of interacting processors of the control facility 20. It should however be noted that different variations are possible for the configuration of the control facility 20. Thus, as will presumably frequently be the case, the measurement data interface 22 and the reconstruction unit 23 can be implemented independently, i.e. not as part of the inventive image data record processing facility 21, in the control facility 20, and the image data record processing facility 21 transfers the necessary image data records from the independent reconstruction unit 23. The reconstruction facility 23 can also output the reconstructed image data records directly by way of a corresponding output interface, for example on the screen 31 or for storage in a memory, e.g. in the memory 29. It is likewise possible for the control facility 20 to have an interface (not shown) with a network connected to the computed tomography system 1, for example a radiological information system (RIS), to store the image data records and/or the projection data records in mass storage devices or to output image data records on printers connected to the network in the form of images selected by the operator or to transfer appropriate weighting factors wCa by way of a network, these already having been supplied for example by manufacturers for certain X-ray system types and certain predefined energy combinations.

Figure 2:
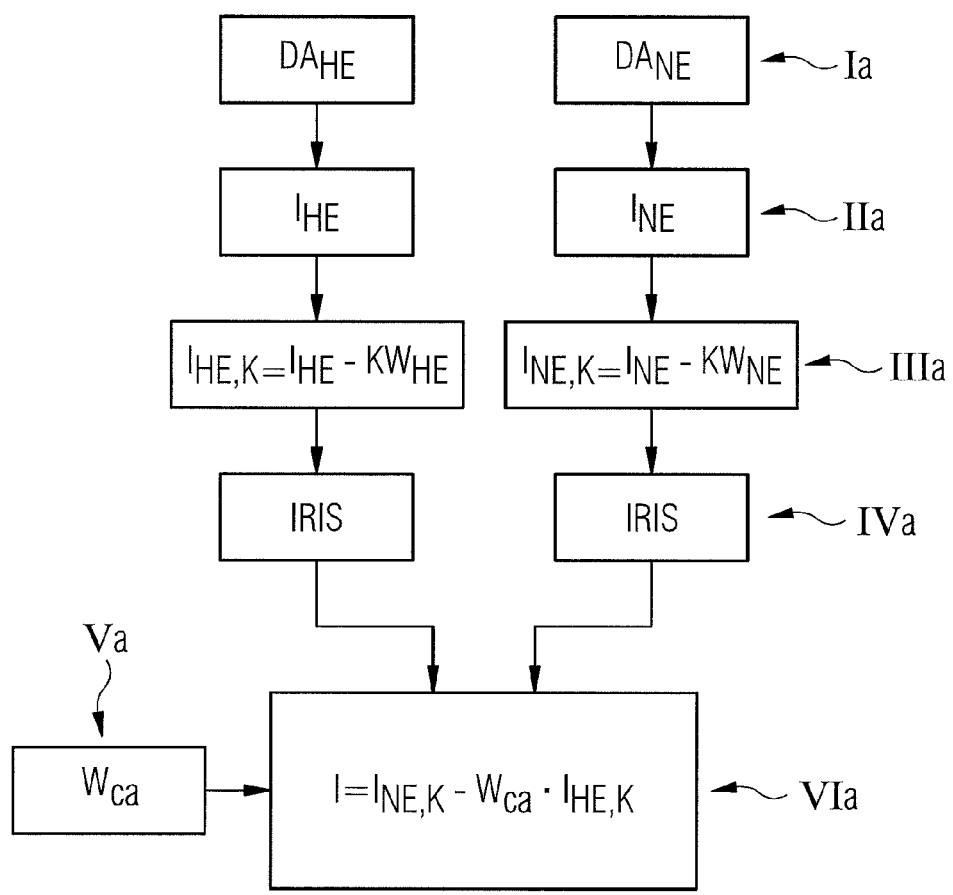
FIG. 2 shows a flow diagram to illustrate a possible method sequence according to a first variant of an embodiment of the inventive method.

The precise mode of operation of the correction unit 25 is described in more detail below with reference to FIGS. 2 and 3, with FIG. 2 showing a particularly simple form of the inventive method and FIG. 3 a more developed variant.

With the method according to FIG. 2 the starting point in step Ia is the transfer of the high-energy projection data record DAHE and the low-energy projection data record DANE. In step IIa a high-energy image data record and a low-energy image data record respectively are reconstructed therefrom. In this process image point values IHE, INE are determined respectively for the individual image points, i.e. in the case of a three-dimensional image data record the individual voxels, the image point values IHE, INE corresponding to the Hounsfield value in the respective voxel with the respective X-ray energy. The image point values, i.e. here the Hounsfield values, each contain information about the material and density of the material in the corresponding voxel. Appropriate reconstruction procedures, such as for example filtered back projection procedures or the like, are known to the person skilled in the art and are therefore not described further here.

As already mentioned above however, this reconstruction does not necessarily have to be part of the inventive method, if for example corresponding image data records with image point values IHE, INE are already available for the individual image points. In this instance the method can start immediately with the transfer of such image data records.

In step IIIa the image point values IHE, INE of the two image data records are first corrected in that the image point values IHE, INE are displaced respectively by a correction value KWHE, KWNE according to the equations $$I_{HE,K} = I_{HE} - KW_{HE} \quad (1a)$$

$$I_{NE,K} = I_{NE} - KW_{NE} \quad (1b).$$

Here IHE,K and INE,K respectively are the corrected image point values of the high-energy image data record and the low-energy image data record and KWHE and KWNE are the correction values for the high-energy image data record and the low-energy image data record.

The correction values KWHE and KWNE are selected so that they correspond roughly to a mean image point value of a base material in the low-energy image data record or high-energy image data record. This base material is generally soft tissue. Since the attenuation in soft tissue is generally largely independent of the X-ray energy, the low-energy correction value KWNE and the high-energy correction value KWHE respectively can be set to an identical value, which for soft tissue is around 40 HU. This correction in step IIIa therefore ensures that the corrected image point values INE,K, IHE,K for soft tissue are approximately equal to 0 in both the low-energy image data record and in the high-energy image data record, so that they are scarcely influenced by the later method step of eliminating the calcium components.

In an optional further method step IVa a further noise-reducing filter IRIS can be applied to the image point values IHE,K, INE,K of the image data records, in order thus to reduce the noise in the images.

Then in a step Va an appropriate weighting factor wCa is selected, which is a function on the one hand of the type of X-ray system 1 used and on the other hand of the X-ray energies used.

In step VIa according to the equation $$I = I_{NE,K} - w_{Ca} \cdot I_{HE,K} \quad (2)$$

corrected image data I is determined from the low-energy image data record and the high-energy image data record. In other words in step IVa the image point values IHE,K of the high-energy image data record, weighted with the weighting factor wCa, are subtracted from the image point values INE,K of the corresponding voxels (i.e. at the same image point position) of the low-energy image data record. According to an embodiment of the invention the weighting factor wCa in step Va is selected so that on subtraction it is the calcium components that are eliminated from the image point values INE, K.

As already mentioned above, the correct weighting factor wCa is a function of both the type of X-ray system and the X-ray energy combination used. It has thus proven for example that for CT systems of the type SOMATOM Definition by Siemens with an energy combination of 80 KV for the low-energy image data record and 140 KV for the high-energy image data record the weighting factor wCa is around 1.4, with an energy combination of 100 KV for the low-energy image data record and 140 KV for the high-energy image data record the weighting factor wCa is in contrast around 1.2. With other device types the weighting factors wCa I are of a similar order. The correct weighting factor wCa can be determined by experiment beforehand for example based on test measurements with phantoms or test subjects, wherein the calcium components are known exactly. It is likewise possible to simulate corresponding measurement for the respective device type in simulation procedures and to use the simulated measurement data thus obtained to determine the weighting factor wCa.

The weighting factor wCa thus determined can then be stored in a storage unit 29 of the control facility 20 of the X-ray system 1. An entire library of appropriate weighting factors wCa for the respective X-ray system is preferably stored at the same time for different energy combinations. The appropriate weighting factor wCa can then be selected automatically as a function of the selected X-ray energy combination and be used within the context of the inventive method. After maintenance work, at least if changes are made to essential components of the geometric dimensions of the data acquisition system, the stored weighting factors are expediently checked again or redetermined.

The corrected image data record generated in step VIa then only contains image point values I, which no longer contain calcium components, so that the problem of calcium blooming described in the introduction no longer plays a role when determining stenoses.

Based on equation 2 the advantage of the correction performed in method step IIIa also becomes immediately visible. If the individual image point values IHE,K and INE,K of the high-energy image data record and the low-energy image data record for the base material (for example soft tissue) are approximately 0, they are scarcely influenced by the weighting factor wCa on subtraction and the base material is shown almost unchanged in the corrected image data record.

It should be noted here that the method steps Ia, IIa, IIIa and IVa shown respectively in parallel in FIG. 2 for the low-energy data record and the high-energy data record can of course also be performed one after the other in any sequence. In other words for example the high-energy image data record is reconstructed first for the high-energy projection data record DAHE, then in step IIIa the correction is performed and then in step IVa filtering and after this for example the same steps are performed for the low-energy projection data record DANE or for example conversely the low-energy projection data record DANE is processed first and then the high-energy projection data record DAHE.

Figure 3:
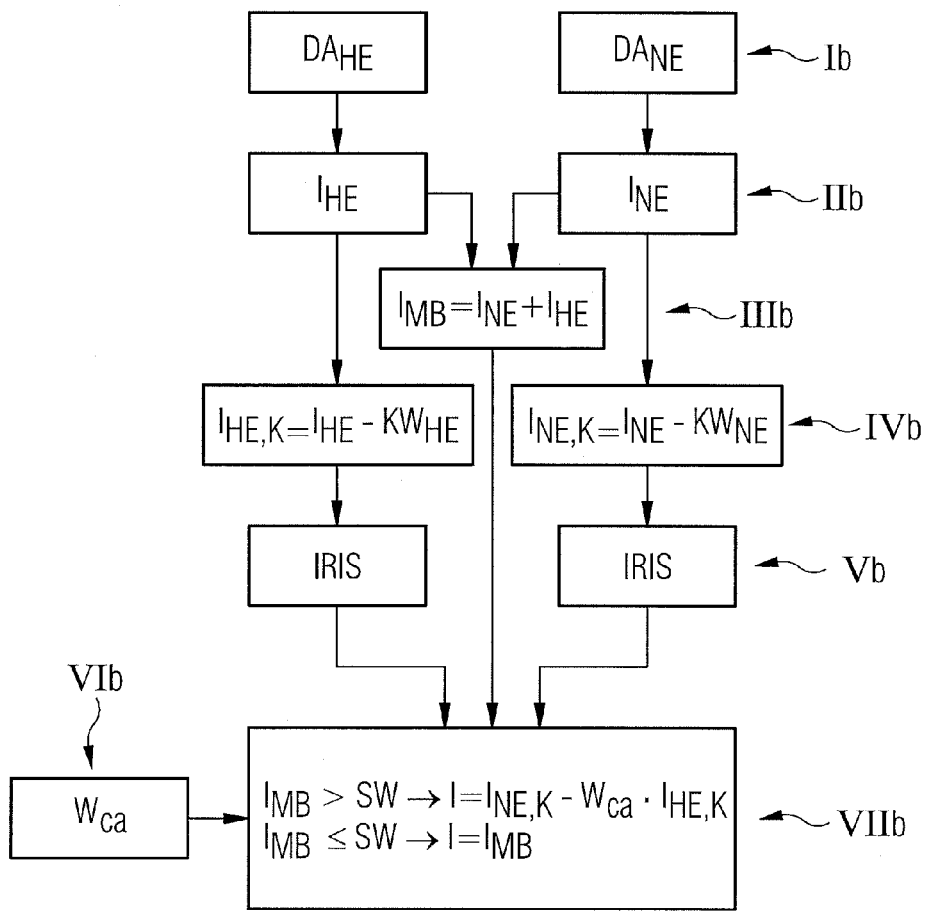
FIG. 3 shows a flow diagram to illustrate a possible method sequence according to a second variant of an embodiment of the inventive method and FIG. 4 in the bottom row shows a number of comparison images from a dual energy measurement of a head, specifically a mixed image (left), a subtraction image according to the first variant of an embodiment of the inventive method (center) and an image according to the second variant of an embodiment of the inventive method (right), and in the top row shows enlarged image segments of each of the images in the bottom row with a vessel to be examined.

FIG. 3 shows an extended variant of the method from FIG. 2. This method also starts in step Ib with the transfer of the projection data records DAHE, DANE and then in step IIb with a reconstruction of the image data records from the projection data records DAHE, DANE. However in a step IIIb a combination image data record, also referred to below as a mixed image, is then first generated, in which the individual image point values INE, IHE of the voxels of the low-energy image data record and the high-energy image data record are added together to generate the image point values IMB of the mixed image.

Otherwise however, as in the method according to FIG. 2, the image point values IHE of the high-energy image data record are first corrected in step IVb as in step IIIa from FIG. 2 and then in step Vb (as in step IVa in FIG. 2) they are optionally processed using a noise reduction filter IRIS. Both method steps are also performed correspondingly for the image point values INE of the low-energy image data record.

Likewise in step VIb (as in step Va of the method according to FIG. 2) an appropriate weighting factor wCa is determined, said weighting factor wCa being the same weighting factor wCa as in the method according to FIG. 2. In contrast to the method according to FIG. 2 however now in step VIIb according to equation (2) a corrected image point value I is only generated by subtraction of the image point value IHE,K of the corrected high-energy image data record weighted with the weighting factor wCa from image point values INE,K of the corrected low-energy image data record, if the image point value IMB of the mixed image is greater than a certain predefined threshold value SW. Otherwise the image point value IMB of the mixed image is taken over as the image point value I for the corrected image data record.

The threshold value SW is preferably selected so that, for example with the CT angiography recordings cited in the introduction, voxels, which have an HU value a long way below the contrast agent, are below the threshold. These are generally voxels from the surrounding soft tissue. Preferably such a threshold is set at 80 HU, particularly preferably 60 HU. This ensures that all the voxels that relate with high probability just to surrounding tissue, not the lumen of the vessels to be examined, which is filled with contrast agent, are not influenced by the inventive subtraction method but contain the information of the mixed image. The background structure, for example fat and soft tissue, therefore remains more clearly visible in the image, for the purposes of orientation and further diagnosis.

Figure 4:
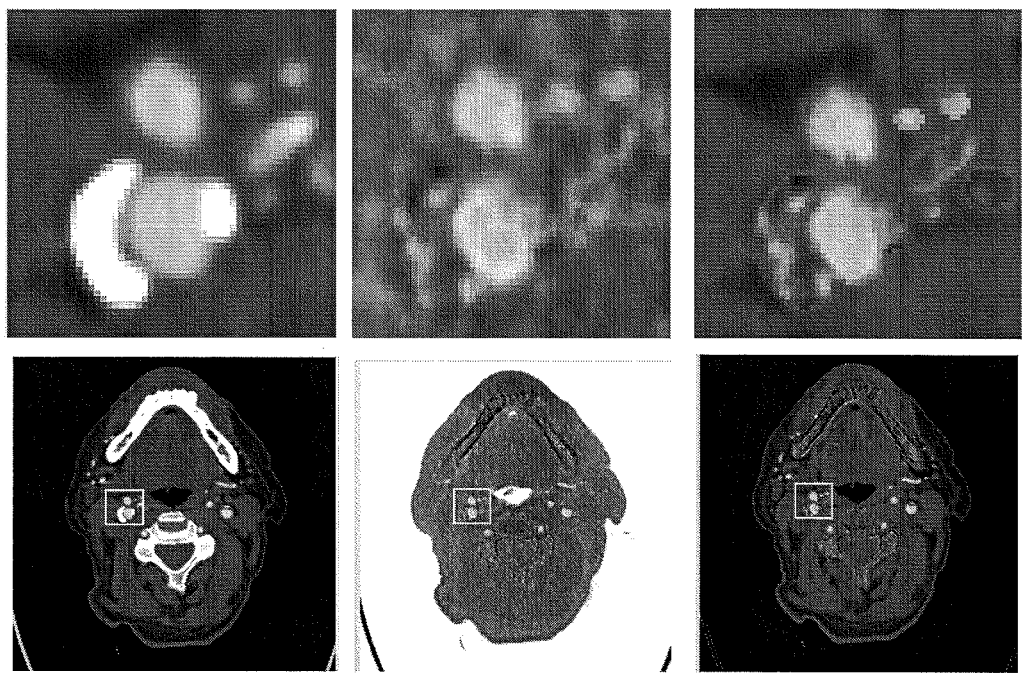

This can be seen in particular in FIG. 4. FIG. 4 shows next to each other from left to right in the bottom row a mixed image, a corrected image according to an embodiment of the method according to FIG. 2 and a corrected image according to the method according to FIG. 3, with all three images having been generated from the same high-energy and low-energy sectional images through a head of a patient. In the top row above each of the images, the segment marked in the lower image is enlarged, showing a section through a vessel affected by a stenosis (in this instance the aorta).

As can be seen from the mixed image and the enlarged image on the left, in a normal mixed image, which only consists of the addition of the high-energy image and the low-energy image, the voxels with a high calcium component stand out strongly. This is due to the calcium blooming (the bright white marks) mentioned in the introduction, which causes the stenosis to appear much more marked than it actually is.

In the center image this calcium blooming is eliminated, so that the degree of stenosis can be determined much more reliably. However the subtraction causes the surrounding tissue to be less clear.

If the threshold-based method is used, as illustrated for example in FIG. 3, the image shown on the right results. Calcium blooming has been removed here too but the surrounding structures in the image are much more clearly visible, as shown in particular in the overview image in the bottom row. It is thus easier for the viewer to find their way round the image and the images can also be used more readily for other diagnoses.

Finally it should be noted once again that the methods and apparatuses described above are only preferred example embodiments of the invention and the invention can be varied by the person skilled in the art without departing from the scope of the invention, in so far as this is predefined by the claims. For the sake of completeness it should also be noted that the use of the indefinite article "a" or "an" does not exclude the possibility of the relevant features also being present in a multiple fashion.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for correcting image data of an examination object, which comprises a first image data record obtained using a first X-ray energy and a second image data record obtained using a second X-ray energy, the method comprising:
generating a corrected image data record by subtracting from image point values at certain image point positions of the first image data record, image point values assigned to the corresponding image point positions in the second image data record, multiplied by a weighting factor, the weighting factor being selected as a function of the first X-ray energy used and the second X-ray energy used so that upon the subtraction, a calcium component is removed from the image point values; and
generating a combination image data record from the first image data record and the second image data record wherein, to generate the corrected image, image point values of the second image data record multiplied by a weighting factor are only subtracted from the image point values of the first image data record at the image point positions where image point values of the combination image data record are relatively greater than a limit value, wherein
before the corrected image data record is generated, at least one of (i) the image point values of the first image data record are each displaced by a first correction value and (ii) the image point values of the second image data record are each displaced by a second correction value, and
at least one of (i) the first correction value corresponds roughly to a mean image point value of a base material in the first image data record, and (ii) the second correction value corresponds roughly to a mean image point value of the base material in the second image data record.

2. The method as claimed in claim 1, wherein the first X-ray energy is relatively lower than the second X-ray energy.

3. The method as claimed in claim 2, wherein the weighting factor is determined as a function of the X-ray system or X-ray system type, which was used to acquire measurement data to obtain the image data.

4. The method as claimed in claim 3, wherein the weighting factor is determined by experiment with the aid of image data based on measurement data, which was acquired with at least one of the same X-ray system or an X-ray system of the same X-ray system type, and/or by way of a simulation of the X-ray system or X-ray system type.

5. A method for generating image data, comprising:
using an X-ray system to perform a first measurement with a first energy, on the basis of which a first image data record is generated;
using the X-ray system to perform a second measurement with a second energy, on the basis of which a second image data record is generated; and
generating a corrected image data record using the method as claimed in claim 2.

6. The method as claimed in claim 1, wherein the image point values at the corresponding image point positions of the combination image data record are taken over as image point values of the corrected image data record at other image point positions.

7. The method as claimed in claim 1, wherein, to generate the combination image data record, image point values at certain image point positions of the first image data record and image point values at the corresponding image point positions of the second image data record are added together.

8. The method as claimed in claim 1, wherein, to generate the image data records, projection data records are recorded in each instance using an X-ray system and the image data records are reconstructed therefrom.

9. The method as claimed in claim 1, wherein the weighting factor is determined as a function of the X-ray system or X-ray system type, which was used to acquire measurement data to obtain the image data.

10. The method as claimed in claim 9, wherein the weighting factor is determined by experiment with the aid of image data based on measurement data, which was acquired with at least one of the same X-ray system or an X-ray system of the same X-ray system type, and/or by way of a simulation of the X-ray system or X-ray system type.

11. A method for generating image data, comprising:
using an X-ray system to perform a first measurement with a first energy, on the basis of which a first image data record is generated;
using the X-ray system to perform a second measurement with a second energy, on the basis of which a second image data record is generated; and
generating a corrected image data record using the method as claimed in claim 1.

12. A non-transitory computer readable medium including program segments for, when executed on a computer device, causing the computer device to implement the method of claim 11.

13. A non-transitory computer readable medium, loadable directly into a memory of an image data record processing facility, including program code segments to execute the method as claimed in claim 1, when the program code segments is are executed in the image data record processing facility.

14. A non-transitory computer readable medium including program segments for, when executed on a computer device, causing the computer device to implement the method of claim 1.

15. An image data record processing facility for correcting image data of an examination object, which comprises a first image data record obtained using a first X-ray energy and a second image data record obtained using a second X-ray energy, the image data record processing facility comprising:
a processor programmed to control interfaces and units to perform functions, the interfaces and units including
an image data interface to transfer the image data records;
an interface to transfer a weighting factor; and
a correction unit to generate a corrected image data record, the correction unit being configured to subtract from image point values, at certain image point positions of the first image data record, image point values which are assigned to the corresponding image point positions of the second image data record, multiplied by the weighting factor, the weighting factor being selected as a function of the first X-ray energy used and the second X-ray energy used, so that a calcium component is eliminated from the image point values on subtraction, the correction unit further being configured to generate a combination image data record from the first image data record and the second image data record wherein, to generate the corrected image data record, image point values of the second image data record multiplied by a weighting factor are only subtracted from the image point values of the first image data record at the image point positions where image point values of the combination image data record are relatively greater than a limit value, wherein
before the corrected image data record is generated, the correction unit is configured to displace at least one of (i) each of the image point values of the first image data record by a first correction value first correction value and (ii) each of the image point values of the second image data record by a second correction value, and
at least one of (i) the first correction value corresponds roughly to a mean image point value of a base material in the first image data record, and (ii) the second correction value corresponds roughly to a mean image point value of the base material in the second image data record.

16. The image data record processing facility as claimed in claim 15, further comprising:
a measurement data interface to transfer projection data records obtained using the X-ray system; and
a reconstruction unit, configured to reconstruct the first image data record from a projection data record of a first measurement and the second image data record from a projection data record of a second measurement.

17. An X-ray system comprising:
at least one X-ray source; and
at least one detector system to acquire projection data records of an examination object and including an image data record processing facility as claimed in claim 16.

18. An X-ray system comprising:
at least one X-ray source; and
at least one detector system to acquire projection data records of an examination object and including an image data record processing facility as claimed in claim 15.

19. A method for correcting image data of an examination object, the image data including a first image data record associated with a first X-ray energy and a second image data record associated with a second X-ray energy, the method comprising:
correcting image point values of the first image data record by a first correction value;
correcting image point values of the second image data record by a second correction value, the first and second correction values being associated with a material in at least one of the first image data record and the second image data record; and
generating a corrected image data record based on the corrected image point values of the first image data and corrected image point values of the second image data, the generating including,
applying a weighting factor to the corrected image point values of the second image data, and
subtracting the weighted corrected image point values of the second image data from the corrected image point values of the first image data, the corrected image data record being based on a result of the subtracting,
wherein at least one of (i) the first correction value corresponds to a mean image point value of the material in the first image data record, and (ii) the second correction value corresponds roughly to a mean image point value of the material in the second image data record.

20. The method of claim 19, wherein the material is soft tissue.

* * * * *